US00PP28155P3

(12) United States Plant Patent
Pieters

(10) Patent No.: US PP28,155 P3
(45) Date of Patent: Jul. 4, 2017

(54) ***CHRYSANTHEMUM* PLANT NAMED 'MIORA ORANGE'**

(50) Latin Name: *Chrysanthemum×morifolium*
Varietal Denomination: Miora Orange

(71) Applicant: Dirk Pieters, Oostnieuwkerke (BE)

(72) Inventor: Dirk Pieters, Oostnieuwkerke (BE)

(73) Assignee: Paraty B.V.B.A., Oostnieuwkerke (BE)

( * ) Notice: Subject to any disclaimer, the term of this patent is extended or adjusted under 35 U.S.C. 154(b) by 149 days.

(21) Appl. No.: 14/545,966

(22) Filed: Jul. 10, 2015

(65) Prior Publication Data

US 2017/0013757 P1 Jan. 12, 2017

(51) Int. Cl.
*A01H 5/02* (2006.01)

(52) U.S. Cl.
USPC ..... Plt./290

(58) Field of Classification Search
USPC ..... Plt./263.1, 286, 287, 290
See application file for complete search history.

*Primary Examiner* — Susan McCormick Ewoldt
*Assistant Examiner* — Karen Redden
(74) *Attorney, Agent, or Firm* — C. A. Whealy

(57) ABSTRACT

A new and distinct cultivar of *Chrysanthemum* plant named 'Miora Orange', characterized by its upright, outwardly spreading and uniformly rounded plant habit; vigorous growth habit; freely branching habit; dense and full plant habit; dark green-colored leaves; uniform and freely flowering habit; and relatively large decorative-type inflorescences with ray florets that are initially red in color becoming dark orange and yellow orange in color with subsequent development giving the inflorescences a bi-colored appearance.

1 Drawing Sheet

Botanical designation: *Chrysanthemum×morifolium.*
Cultivar denomination: 'MIORA ORANGE'.

BACKGROUND OF THE INVENTION

The present invention relates to a new and distinct cultivar of *Chrysanthemum* plant, botanically known as *Chrysanthemum×morifolium* and hereinafter referred to by the name 'Miora Orange'.

The new *Chrysanthemum* plant is a product of a planned breeding program conducted by the Inventor in Oostnieuwkerke, Belgium. The objective of the breeding program is to create new uniformly mounding and freely flowering *Chrysanthemum* plants with unique and attractive ray floret coloration.

The new *Chrysanthemum* plant originated from a cross-pollination made by the Inventor in Oostnieuwkerke, Belgium in October, 2009 of *Chrysanthemum×morifolium* 'Caprioli Orange', not patented, as the female, or seed, parent with *Chrysanthemum×morifolium* 'Kismo Orange', not patented. The new *Chrysanthemum* plant was discovered and selected by the Inventor as a flowering plant from within the progeny of the stated cross-pollination in a controlled greenhouse environment in Oostnieuwkerke, Belgium in September, 2010.

Asexual reproduction of the new *Chrysanthemum* plant by vegetative terminal cuttings was first conducted in a controlled greenhouse environment in Oostnieuwkerke, Belgium in January, 2011. Asexual reproduction by vegetative terminal cuttings has shown that the unique features of this new *Chrysanthemum* plant are stable and reproduced true to type in successive generations.

SUMMARY OF THE INVENTION

Plants of the new *Chrysanthemum* have not been observed under all possible combinations of environmental conditions and cultural practices. The phenotype may vary somewhat with variations in environmental conditions such as temperature, daylength and light intensity, without, however, any variance in genotype.

The following traits have been repeatedly observed and are determined to be the unique characteristics of 'Miora Orange'. These characteristics in combination distinguish 'Miora Orange' as a new and distinct *Chrysanthemum* plant:

1. Upright, outwardly spreading and uniformly rounded plant habit; vigorous growth habit.
2. Freely branching habit; dense and full plant habit.
3. Dark green-colored leaves.
4. Uniform and freely flowering habit.
5. Relatively large decorative-type inflorescences with ray florets that are initially red in color becoming dark orange and yellow orange in color with subsequent development giving the inflorescences a bi-colored appearance.

Plants of the new *Chrysanthemum* differ from the female parent, 'Caprioli Orange', in the following characteristics:

1. Plants of the new *Chrysanthemum* are smaller than plants of 'Caprioli Orange'.
2. Plants of the new *Chrysanthemum* and 'Caprioli Orange' differ in ray floret color as inflorescences of plants of 'Caprioli Orange' have dark orange-colored ray florets.

Plants of the new *Chrysanthemum* differ from the male parent, 'Kismo Orange', in the following characteristics:

1. Plants of the new *Chrysanthemum* are more compact than plants of 'Kismo Orange'.
2. Plants of the new *Chrysanthemum* have broader leaves than plants of 'Kismo Orange'.
3. Plants of the new *Chrysanthemum* have larger inflorescences than plants of 'Kismo Orange'.

4. Plants of the new *Chrysanthemum* and 'Kismo Orange' differ in ray floret color as inflorescences of plants of 'Kismo Orange' have light orange to salmon orange-colored ray florets.

Plants of the new *Chrysanthemum* can be compared to plants of *Chrysanthemum×morifolium* 'Nerola Orange', disclosed in U.S. Plant Pat. No. 23,274. In side-by-side comparisons conducted in Oostnieuwkerke, Belgium, plants of the new *Chrysanthemum* differed from plants of 'Nerola Orange' in the following characteristics:

1. Plants of the new *Chrysanthemum* were more compact than plants of 'Nerola Orange'.
2. Plants of the new *Chrysanthemum* and 'Nerola Orange' differed in overall plant shape plants of the new *Chrysanthemum* were flatter than and not as spherical as plants of 'Nerola Orange'.
3. Leaves of plants of the new *Chrysanthemum* were broader and not as dark green in color as leaves of plants of 'Nerola Orange'.

BRIEF DESCRIPTION OF THE PHOTOGRAPH

The accompanying photograph illustrates the overall appearance of the new *Chrysanthemum* plant showing the colors as true as it is reasonably possible to obtain in colored reproductions of this type. Colors in the photograph may differ slightly from the color values cited in the detailed botanical description which accurately describe the colors of the new *Chrysanthemum* plant.

The photograph comprises a side perspective view of a typical flowering plant of 'Miora Orange' grown in a container.

DETAILED BOTANICAL DESCRIPTION

The aforementioned photograph and following observations and measurements describe plants grown in 19-cm containers in an outdoor nursery in Oostnieuwkerke, Belgium during the spring and summer and under cultural practices generally used in commercial *Chrysanthemum* production. During the production of the plants, day temperatures ranged from 18° C. to 21° C. and night temperatures ranged from 10° C. to 15° C. Plants were 20 weeks old when the photograph and description were taken. In the following description, color references are made to The Royal Horticultural Society Colour Chart, 2005 Edition, except where general terms of ordinary dictionary significance are used.

Botanical classification: *Chrysanthemum×morifolium* 'Miora Orange'.

Parentage:

*Female, or seed, parent.*—*Chrysanthemum×morifolium* 'Caprioli Orange', not patented.

*Male, or pollen, parent.*—*Chrysanthemum×morifolium* 'Kismo Orange', not patented.

Propagation:

*Type.*—Vegetative terminal cuttings.

*Time to initiate roots, summer.*—About 14 days at temperatures about 20° C.

*Time to initiate roots, winter.*—About 20 days at temperatures about 20° C.

*Time to produce a rooted young plant, summer.*—About 30 days at temperatures about 20° C.

*Time to produce a rooted young plant, winter.*—About 40 days at temperatures about 20° C.

*Root description.*—Fine, fibrous; typically light brown in color, actual color of the roots dependent on substrate composition, water quality, fertilizers, substrate temperature and age of roots.

*Rooting habit.*—Freely branching; medium density.

Plant description:

*Appearance.*—Perennial decorative-type *Chrysanthemum*; stems upright and outwardly spreading giving a uniformly rounded appearance to the plant; plants nearly spherical in overall shape, somewhat flattened; very freely branching habit, about 25 to 30 primary lateral branches develop, each primary lateral branch with multiple secondary branches; pinching enhances lateral branch development; dense and full plant habit; strong and vigorous growth habit.

*Plant height.*—About 35 cm.

*Plant width.*—About 45 cm.

*Lateral branches.*—Length: About 30 cm to 35 cm. Diameter: About 2 mm to 3 mm. Internode length: About 2 cm to 2.5 cm. Strength: Strong, flexible. Aspect: Upright to outwardly spreading. Texture: Pubescent; longitudinally ridged. Luster: Matte. Color: Close to 136A.

*Leaves.*—Arrangement: Alternate, simple. Length: About 4 cm to 6 cm. Width: About 3.5 cm to 4 cm. Apex: Rounded to cuspidate. Base: Attenuate. Margin: Palmately lobed and serrate, sinuses between lateral lobes divergent to parallel. Texture, upper and lower surfaces: Slightly pubescent. Luster, upper and lower surfaces: Matte. Color: Developing leaves, upper surface: Close to 137A. Developing leaves, lower surface: Close to 137C. Fully expanded leaves, upper surface: Close to 136A; venation, close to 148C. Fully expanded leaves, lower surface: Close to 137C; venation, close to 147B to 147C. Petioles: Length: About 1 cm. Diameter: About 2 mm. Texture, upper and lower surfaces: Slightly pubescent and slightly rough. Luster, upper and lower surfaces: Matte. Color, upper surface: Close to 136A. Color, lower surface: Close to 137C.

Inflorescence description:

*Appearance.*—Decorative-type inflorescence form; inflorescences borne on terminals above foliar plane; disc and ray florets arranged acropetally on a capitulum.

*Fragrance.*—Faintly fragrant, pungent.

*Flowering time.*—Under natural season conditions, plants flower in mid-September in Belgium.

*Postproduction longevity.*—Inflorescences maintain good color and substance for about 45 to 49 days on the plant grown in an outdoor nursery; inflorescences persistent.

*Quantity of inflorescences.*—Freely flowering habit with about 30 inflorescences developing per lateral branch with numerous inflorescences developing per plant.

*Inflorescence buds.*—Height: About 6 mm. Diameter: About 8 mm. Shape: Globular. Texture: Smooth. Color: Close to 137A.

*Inflorescence size and shape.*—Diameter: Relatively large, about 5 cm. Depth (height): About 3.5 cm. Disc diameter: About 3 mm. Shape: Circular; raised dome. Receptacle diameter: About 3 mm. Receptacle height: About 2.5 mm to 3 mm. Receptacle texture: Smooth, glabrous. Receptacle color: Close to 144B.

*Ray florets.*—Quantity and arrangement: About or more than 200 ray florets per inflorescence arranged in about ten whorls. Length: About 1.5 cm to 2 cm. Width: About 5 mm. Shape: Oval. Apex: Rounded. Base: Attenuate. Margin: Entire. Aspect: Mostly flat. Texture, upper and lower surfaces: Smooth, glabrous. Luster, upper and lower surfaces: Matte. Color: When opening, upper surface: Close to 179A. When opening, lower surface: Close to 171B. Fully opened, upper surface: Close to 171B; color becoming closer to 20A with development. Fully opened, lower surface: Close to 167B; color becoming closer to 20B with development.

*Disc florets.*—Quantity and arrangement: About 40 disc florets per inflorescence and massed at the center of the receptacle; disc florets inconspicuous. Length: About 3 mm. Diameter: About 0.5 mm to 1 mm. Shape: Tubular, elongated; apices acute. Color, immature: Apex: Close to 145A. Mid-section: Close to 145A. Base: Close to 145A. Color, mature: Apex: Close to 12A. Mid-section: Close to 12A. Base: Close to 12A.

*Phyllaries*.—Quantity and arrangement: About 25 phyllaries per inflorescence arranged in about two or three whorls. Length: About 4 mm to 6 mm. Width: About 2 mm to 3 mm. Shape: Ovate. Apex: Rounded. Base: Rounded to truncate. Margin: Entire. Texture, upper and lower surfaces: Smooth, glabrous. Luster, upper and lower surfaces: Matte. Color, upper surface: Close to 137A. Color, lower surface: Close to N137B.

*Peduncles.*—Length, terminal peduncle: About 6 cm. Length, fourth peduncle: About 6 cm. Length, seventh peduncle: About 6 cm. Diameter: About 2 mm. Angle: About 30° from vertical. Strength: Moderately strong. Texture: Slightly pubescent. Luster: Matte. Color: Close to 136A.

*Reproductive organs.*—Androecium: None observed. Gynoecium: None observed.

*Seeds and fruit.*—Seed and fruit production have not been observed on plants of the new *Chrysanthemum.*

Disease & pest resistance: Resistance to pathogens and pests common to *Chrysanthemum* plants has not been observed on plants of the new *Chrysanthemum* grown under commercial production conditions.

Garden performance: Plants of the new *Chrysanthemum* have demonstrated excellent garden performance and will tolerate temperatures ranging from about 0° C. to about 45° C.

It is claimed:

1. A new and distinct *Chrysanthemum* plant named 'Miora Orange' as illustrated and described.

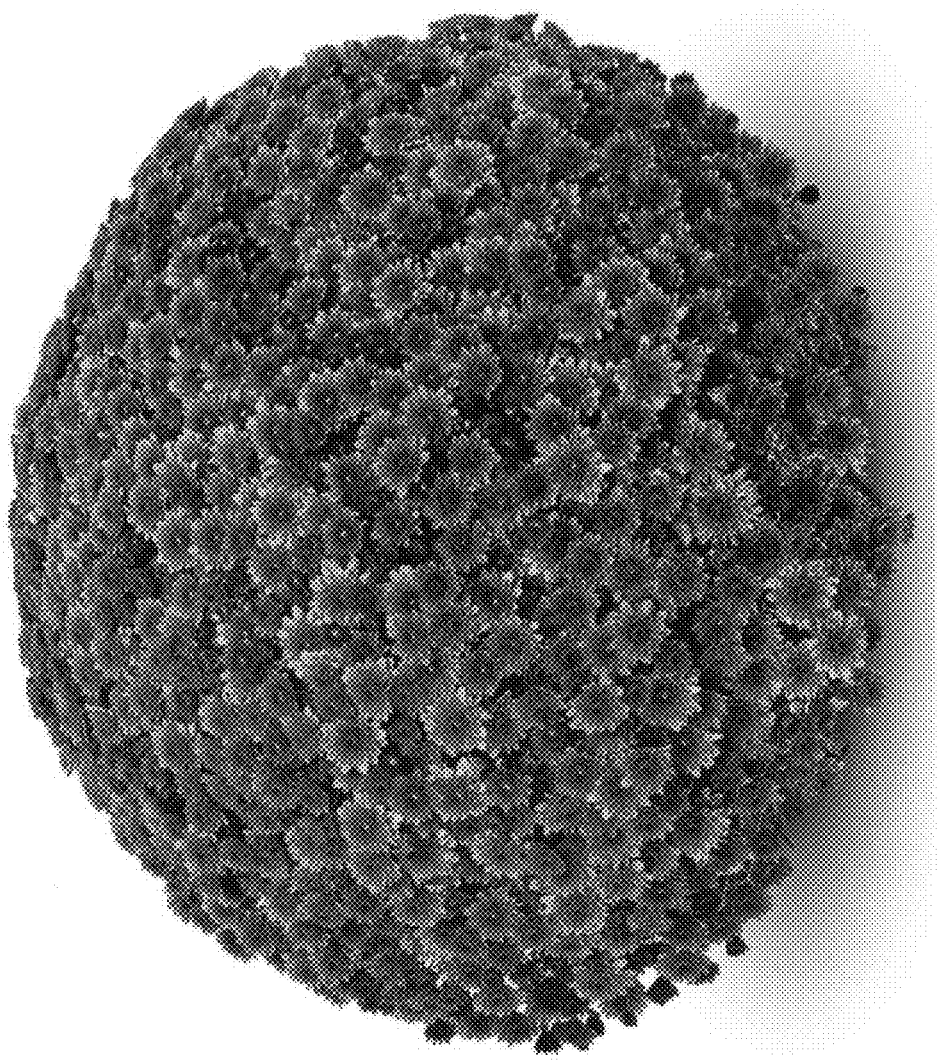

* * * * *